(12) United States Patent
Buschmann et al.

(10) Patent No.: US 7,763,754 B2
(45) Date of Patent: Jul. 27, 2010

(54) PROCESS FOR PRODUCING (1RS,3RS,6RS)-6-DIMETHYL AMINOMETHYL-1-(3-METHOXYPHENYL)-CYCLOHEXANE-1,3-DIOL

(75) Inventors: Helmut Heinrich Buschmann, Aachen (DE); Wolfgang Hell, Aachen (DE); Joerg Holenz, Enhoerna (SE); Oswald Zimmer, Wuerselen (DE); Irene Vaulont, Buchs (CH); Dieter Haag, Radolfzell-Guettingen (DE); Emad El Sayed, Zumikon (CH); Robert Hett, Unteraegeri (CH); Alfed Olbrich, Halle/Westf. (DE); Lars Pumpenmeier, Bielefeld (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/394,758

(22) Filed: Feb. 27, 2009

(65) Prior Publication Data

US 2009/0253936 A1    Oct. 8, 2009

(30) Foreign Application Priority Data

Feb. 29, 2008 (EP) .................................. 08003842

(51) Int. Cl.
C07C 209/66 (2006.01)

(52) U.S. Cl. ....................... 564/455; 564/443

(58) Field of Classification Search ....................... None
See application file for complete search history.

(56) References Cited

U.S. PATENT DOCUMENTS

| 5,733,936 A | 3/1998 | Buschmann et al. |
| 5,801,201 A | 9/1998 | Graudums et al. |
| 6,890,959 B2 * | 5/2005 | Puetz et al. ................. 514/657 |

FOREIGN PATENT DOCUMENTS

| EP | 0 753 506 B1 | 1/1997 |
| EP | 0 780 369 A | 6/1997 |
| WO | WO 01/49651 A | 7/2001 |

OTHER PUBLICATIONS

Turnbull et al., Stereochemical Control in the Synthesis of the Cyclohexyl Portion of the Milbemycin Skeleton, *Tetrahedron Letters*, vol. 25, No. 47, pp. 5449-5452, 1984.
Deboer, Vapor-Phase Introduction of Vinyl Ketones in Michael Additions, *Journal of Organic Chemistry*, vol. 39, No. 16, 1974.
International Search Report, mailed Apr. 17, 2009, with English translation, seven (7) pages.

* cited by examiner

*Primary Examiner*—Brian J Davis
(74) *Attorney, Agent, or Firm*—Crowell & Moring LLP

(57) ABSTRACT

A process for producing (1R,3R,6R)-6-dimethylaminomethyl-1-(3-methoxyphenyl)-cyclohexane-1,3-diol or (1S,3S,6S)-6-dimethylaminomethyl-1-(3-methoxyphenyl)-cyclohexane-1,3-diol or mixtures thereof.

12 Claims, No Drawings

PROCESS FOR PRODUCING (1RS,3RS,6RS)-6-DIMETHYLAMINOMETHYL-1-(3-METHOXYPHENYL)-CYCLOHEXANE-1,3-DIOL

BACKGROUND OF THE INVENTION

The present invention relates to a process for producing (1R,3R,6R)-6-dimethylaminomethyl-1-(3-methoxyphenyl)-cyclohexane-1,3-diol or (1S,3S,6S)-6-dimethylaminomethyl-1-(3-methoxyphenyl)-cyclohexane-1,3-diol or mixtures thereof.

U.S. Pat. No. 5,733,936 (=EP 753,506) discloses 6-dimethylaminomethyl-1-(3-hydroxy- or 3-$C_1$-$C_4$-alkoxyphenyl)-cyclohexane-1,3-diols which are suitable for use as pharmacologically effective analgesics for the treatment of pain. These compounds are chiral and have 3 asymmetric carbon atoms. These 6-dimethylaminomethyl-1-(3-hydroxy- or 3-$C_1$-$C_4$-alkoxyphenyl)-cyclohexane-1,3-diols are produced in a multi-step process by means of a protecting group strategy (introduction and splitting of ketal groups) and subsequent hydrogenation.

It has been found that some stereoisomers are characterized by particularly good pharmacological efficacy. These stereoisomers are the (1R,3R,6R)- and (1S,3S,6S)-stereoisomers of formulas (Va) and (Vb) or mixtures thereof:

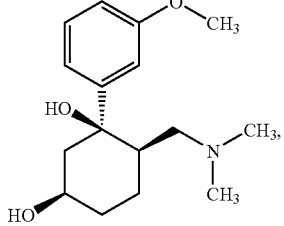
(Va)

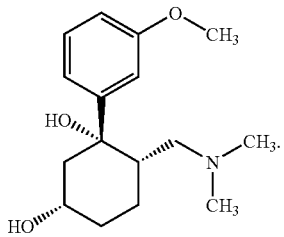
(Vb)

The (1R,3R,6R)- and (1S,3S,6S)-stereoisomers of formulas (Vc) and (Vd)

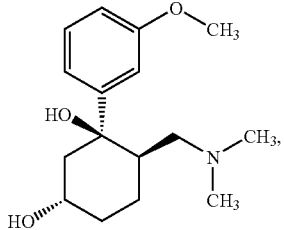
(Vc)

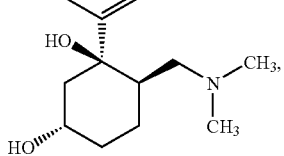
(Vd)

are, in contrast, less desirable and their formation should thus be avoided as far as possible during the production process.

SUMMARY OF THE INVENTION

An object of the present invention was to provide a process for the targeted production of stereoisomers of formulas (Va) and (Vb) or mixtures thereof, in which the formation of by-products, including the undesirable stereoisomers (Vc) and (Vd), and/or of decomposition products is avoided as far as possible.

A further object of the present invention was to provide a process for producing the stereoisomers (Va) and (Vb) which can be carried out without the use of protective groups.

These and other objects of the present invention have been achieved by providing a process for producing (1R,3R,6R)-6-dimethylaminomethyl-1-(3-methoxyphenyl)-cyclohexane-1,3-diol or (1S,3S,6S)-6-dimethylaminomethyl-1-(3-methoxyphenyl)-cyclohexane-1,3-diol or mixtures thereof, respectively, in the form of a free base or as an acid addition salt, comprising at least the following steps:

(b) reacting 3-dimethylamino-1-(3-methoxyphenyl)-propan-1-one (II)

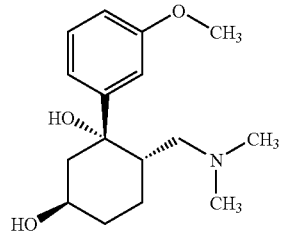
(II)

to form 2-dimethylaminomethyl-1-(3-methoxyphenyl)hexane-1,5-dione (III)

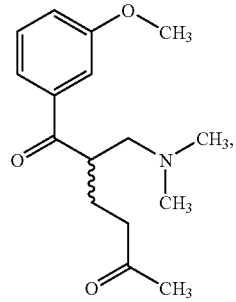
(III)

and (c) cyclizing 2-dimethylaminomethyl-1-(3-methoxyphenyl)hexane-1,5-dione (III) to form 4-dimethylaminomethyl-3-hydroxy-3-(3-methoxyphenyl)cyclohexanone (IV)

(IV)

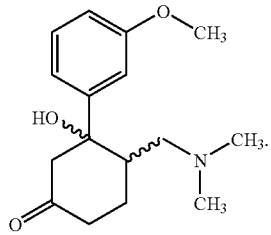

In a further embodiment, the process according to the invention also comprises the following step (a) reacting 3-methoxyacetophenone (I)

(I)

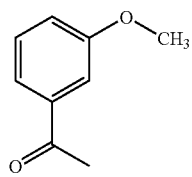

to form 3-dimethylamino-1-(3-methoxyphenyl)-propan-1-one (II)

(II)

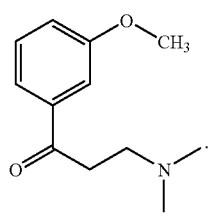

In a further embodiment, the process according to the invention also comprises the following step(s):

(d) reducing 4-dimethylaminomethyl-3-hydroxy-3-(3-methoxyphenyl)cyclohexanone (IV) to form (1R,3R,6R)-6-dimethylaminomethyl-1-(3-methoxyphenyl)cyclohexane-1,3-diol (Va) or (1S,3S,6S)-6-dimethylaminomethyl-1-(3-methoxyphenyl)-cyclohexane-1,3-diol (Vb) or mixtures thereof (Va)

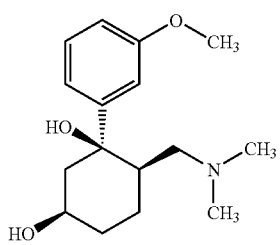

(Vb)

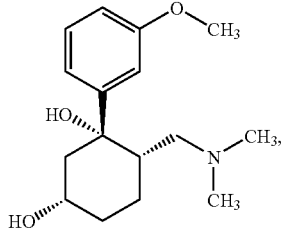

and (e) optionally reacting (1R,3R,6R)-6-dimethylaminomethyl-1-(3-methoxyphenyl)-cyclohexane-1,3-diol (Va) or (1S,3S,6S)-6-dimethylaminomethyl-1-(3-methoxy-phenyl)cyclohexane-1,3-diol (Vb) or a mixture thereof to form the corresponding acid addition salt.

In a preferred embodiment of the process according to the invention, the reaction steps may thus have the following results:

(a) reacting 3-methoxyacetophenone (I)

(I)

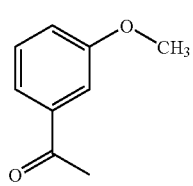

to form 3-dimethylamino-1-(3-methoxyphenyl)propan-1-one (II) as a free base or acid addition salt, (II)

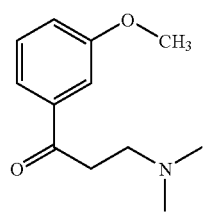

(b) reacting 3-dimethylamino-1-(3-methoxyphenyl)propan-1-one (II) to form 2-dimethylaminomethyl-1-(3-methoxyphenyl)hexane-1,5-dione (III), (III)

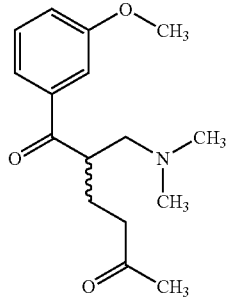

(c) cyclizing 2-dimethylaminomethyl-1-(3-methoxyphenyl)hexane-1,5-dione (III) to form 4-dimethylaminomethyl-3-hydroxy-3-(3-methoxyphenyl)cyclohexanone (IV),

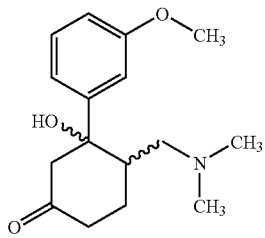
(IV)

(d) reducing 4-dimethylaminomethyl-3-hydroxy-3-(3-methoxyphenyl)cyclohexanone (IV) to form (1R,3R,6R)-6-dimethylaminomethyl-1-(3-methoxyphenyl)cyclohexane-1,3-diol (Va) or (1S,3S,6S)-6-dimethylaminomethyl-1-(3-methoxyphenyl)cyclohexane-1,3-diol (Vb) or mixtures thereof, and

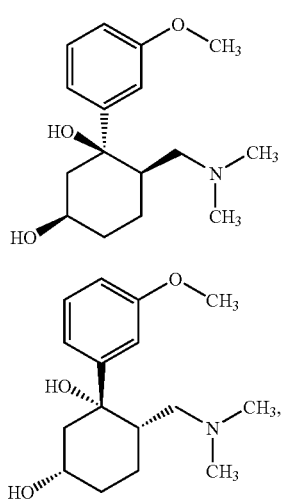

(e) optionally reacting (1R,3R,6R)-6-dimethylaminomethyl-1-(3-methoxyphenyl)-cyclohexane-1,3-diol (Va) or (1S,3S,6S)-6-dimethylaminomethyl-1-(3-methoxyphenyl)cyclohexane-1,3-diol (Vb) or a mixture thereof to form the corresponding acid addition salts.

Surprisingly, it has been found that it is possible to achieve the targeted production of stereoisomers of formulas (Va) and (Vb) or mixtures thereof and that, with good to high conversion rates and yields, it is possible to obtain good levels of selectivity and purity using the process according to the invention if 2-dimethylaminomethyl-1-(3-methoxyphenyl)hexane-1,5-dione (III) is cyclized in the presence of bases to form 4-dimethylaminomethyl-3-hydroxy-3-(3-methoxyphenyl)-cyclohexanone (IV).

Furthermore, it has also surprisingly been found that the synthesis steps (b) and (c) may be carried out in a one-pot process, i.e. preferably without isolating the compound (III), the economic feasibility of the process according to the invention being further improved.

The individual process steps are shown in the following Diagram 1:

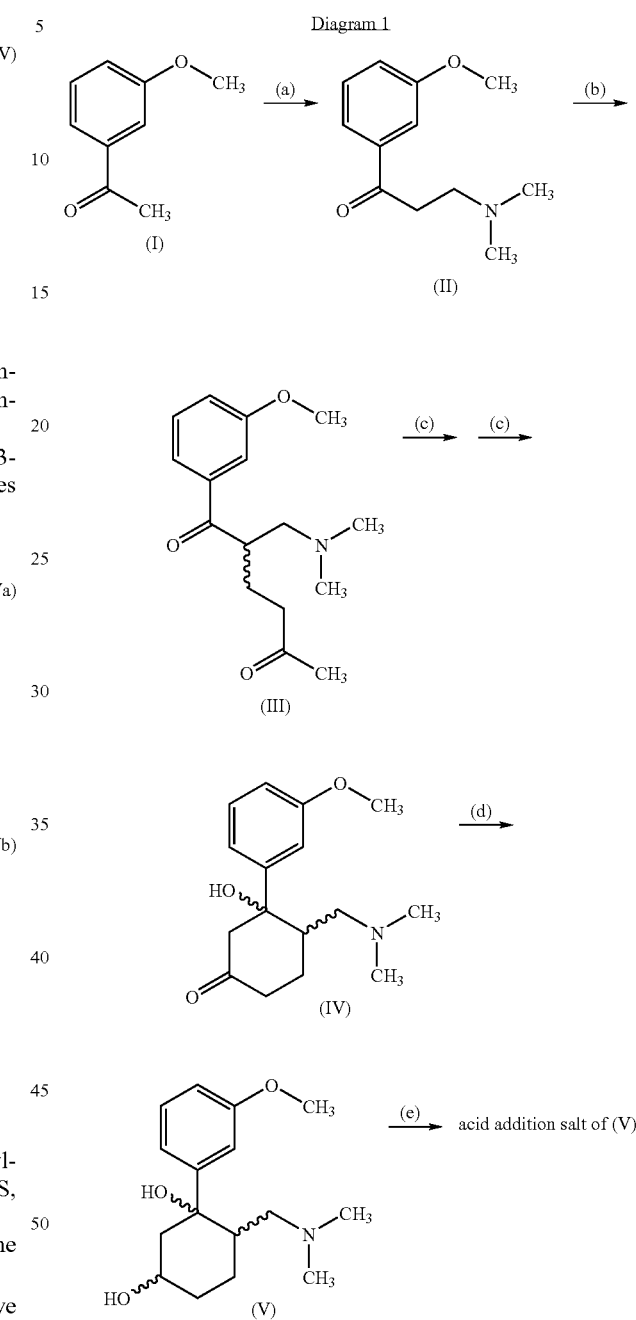

The absolute and relative configurations of the asymmetric carbon atoms of the chiral compounds (III), (IV) and (V) are not shown in Diagram 1.

In Diagram 1 the structural formula shown for chiral compound (III) represents the enantiomer-pure compound (R)-2-dimethylaminomethyl)-1-(3-methoxyphenyl)-hexane-1,5-dione of formula (IIIa) or the enantiomer-pure compound (S)-2-dimethyl-aminomethyl)-1-(3-methoxyphenyl)hexane-1,5-dione of formula (IIIb) or a mixture of the two enantiomers (IIIa) and (IIIb) in any ratio (racemate, mixture of enantiomers):

(IIIa)

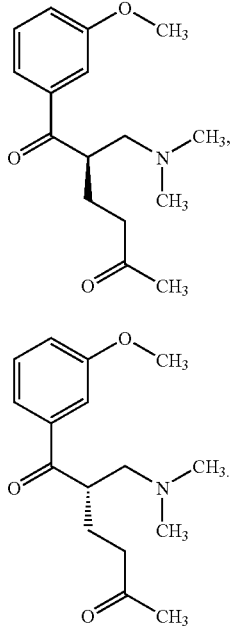

(IIIb)

In particular, the compounds of formulas (IIIa) and (IIIb) are in the form of a substantially racemic mixture.

Furthermore, the structural formula shown in Diagram 1 of the chiral compound (IV) represents, for the respective enantiomer-pure compounds, (3R,4R)-4-dimethylaminomethyl-3-hydroxy-3-(3-methoxyphenyl)cyclohexanone (IVa), (3S,4S)-4-dimethylaminomethyl-3-hydroxy-3-(3-methoxyphenyl)cyclohexanone (IVb), (3R,4S)-4-dimethylaminomethyl-3-hydroxy-3-(3-methoxyphenyl)cyclohexanone (IVc) or (3S,4R)-4-dimethylaminomethyl-3-hydroxy-3-(3-methoxyphenyl)cyclohexanone (IVd) or a mixture of these chiral compounds in any ratio (racemates, mixtures of enantiomers, mixtures of diastereomers, mixtures of epimers):

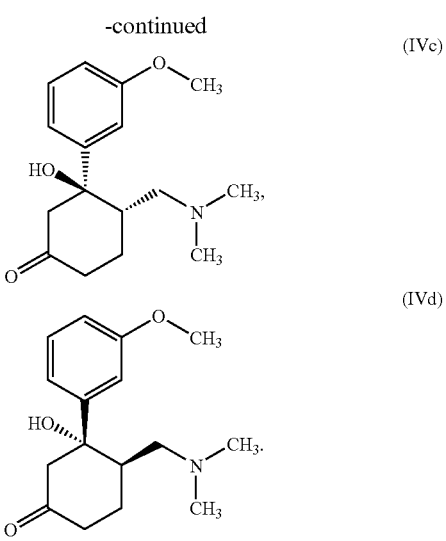

In particular, the compounds of formulas (IV) are in the form of a substantially racemic mixture of compounds (IVa) and (IVb).

Furthermore, the structural formula shown in Diagram 1 of the chiral compound (V) represents, for the respective enantiomer-pure compounds (1R,3R,6R)-6-dimethylaminomethyl-1-(3-methoxyphenyl)cyclohexane-1,3-diol (Va), (1S,3S,6S)-6-dimethylaminomethyl-1-(3-methoxyphenyl)cyclohexane-1,3-diol (Vb), (1R,3S,6R)-6-dimethylaminomethyl-1-(3-methoxyphenyl)cyclohexane-1,3-diol (Vc), (1S,3R,6S)-6-dimethylaminomethyl-1-(3-methoxyphenyl)cyclohexane-1,3-diol (Vd), (1R,3R,6S)-6-dimethylaminomethyl-1-(3-methoxyphenyl)cyclohexane-1,3-diol (Ve), (1S,3S,6R)-6-dimethylaminomethyl-1-(3-methoxyphenyl)cyclohexane-1,3-diol (Vf), (1R,3S,6S)-6-dimethylaminomethyl-1-(3-methoxyphenyl)cyclohexane-1,3-diol) (Vg) or (1S,3R,6R)-6-dimethylaminomethyl-1-(3-methoxyphenyl)cyclohexane-1,3-diol (Vh) or a mixture of these chiral compounds in any ratio (racemates, mixtures of enantiomers, mixtures of diastereomers, mixtures of epimers):

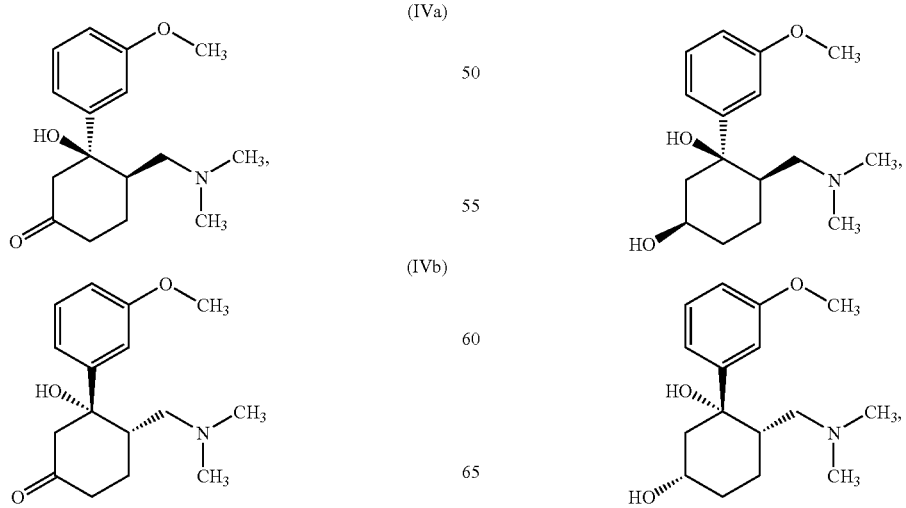

-continued

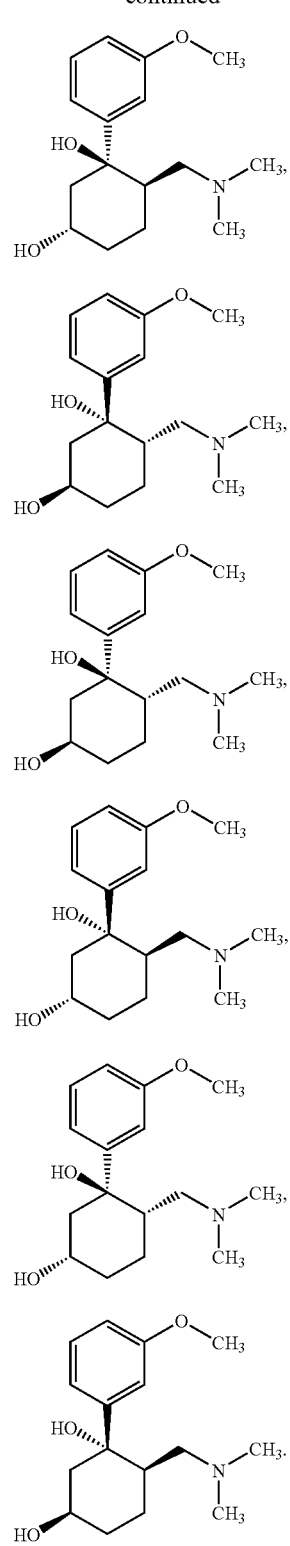

(Vc)

(Vd)

(Ve)

(Vf)

(Vg)

(Vh)

The process disclosed herein is used, in particular, to produce the chiral compounds (Va) or (Vb) or a mixture thereof, which have favourable analgesic properties. In particular, compounds (Va) or (Vb) are in the form of a substantially racemic mixture.

Synthesis step (a) is preferably carried out as a Mannich reaction. In a preferred embodiment of the Mannich reaction, 3-methoxyacetophenone (I) may be reacted with tetramethyl diaminomethane and acetyl chloride.

In another preferred embodiment of the Mannich reaction, 3-methoxyacetophenone (I) may be reacted with paraformaldehyde and dimethylamine hydrochloride.

It is known to persons skilled in the art that the tetramethyl diaminomethane and acetyl chloride components used, or the paraformaldehyde and dimethylamine hydrochloride components used first form an iminium salt which then reacts with 3-methoxyacetophenone (I). These iminium salts are referred to hereinafter as Eschenmoser salt. Eschenmoser salt is preferably to be understood as an iminium salt obtained by reacting tetramethyl diaminomethane with acetyl chloride.

In a preferred embodiment of the process according to the invention the Eschenmoser salt can first be produced and then either undissolved or dissolved 3-methoxyacetophenone (I) may be added to the solution or suspension of the Eschenmoser salt, or the solution or suspension of the Eschenmoser salt may be added to undissolved or dissolved 3-methoxyphenone (I).

In a particularly preferred embodiment, undissolved or dissolved 3-methoxyacetophenone (I) may be added to a solution or suspension of the Eschenmoser salt.

The Eschenmoser salt may be produced in a conventional solvent (reaction medium) known to the person skilled in the art, it being possible to use dimethylformamide, acetonitrile, isopropanol or mixtures of at least two of these solvents in particular. The Eschenmoser salt is preferably produced in acetonitrile.

If the Eschenmoser salt is produced from tetramethyl diaminomethane and acetyl chloride, the amount of substance ratio of tetramethyl diaminomethane to acetyl chloride is preferably from 10:1 to 1:10, more preferably from 8:1 to 1:8, even more preferably from 6:1 to 1:6, most preferably from 4:1 to 1:4 and in particular from 2:1 to 1:2. In a particularly preferred embodiment tetramethyl diaminomethane and acetyl chloride are used in substantially equimolar substance amounts (substance amount ratio=1:1).

If the Eschenmoser salt is produced from paraformaldehyde and dimethylamine hydrochloride, the substance amount ratio of paraformaldehyde to dimethylamine hydrochloride is preferably from 10:1 to 1:10, more preferably from 8:1 to 1:8, even more preferably from 6:1 to 1:6, most preferably from 4:1 to 1:4 and in particular from 2:1 to 1:2. In a preferred embodiment paraformaldehyde and dimethylamine hydrochloride are used in substantially equimolar substance amounts (substance amount ratio=1:1).

It is also known to the person skilled in the art that paraformaldehyde, dimethylamine and hydrochloric acid may also be used to produce Eschenmoser salt. This corresponds to the reaction between paraformaldehyde and dimethylamine hydrochloride. In this instance, the substance amount ratio of hydrochloric acid to dimethylamine is preferably from 10:1 to 1:10, more preferably from 6:1 to 1:6, even more preferably from 4:1 to 1:4, particularly preferably from 3:1 to 1:3, most preferably from 2:1 to 1:2 and in particular 1:1.

In a preferred embodiment the Eschenmoser salt is synthesized independently of the selected components, which are selected in order to produce the Eschenmoser salt, under reflux. It is thus known to the person skilled in the art that the reflux temperature depends on the solvent selected and on environmental variables (for example pressure).

In another preferred embodiment the Eschenmoser salt may be produced at a reaction temperature preferably of from −10 to 100° C., more preferably from 0 to 80° C., even more preferably from 10 to 60° C., most preferably from 20 to 30° C. and in particular from 20 to 25° C.

The resulting Eschenmoser salt may be present in a solvent, preferably dissolved or suspended. In a particularly preferred embodiment the Eschenmoser salt is present as a suspension in acetonitrile.

The reaction time for producing the Eschenmoser salt is preferably from 1 minute to 16 hours, more preferably from 5 minutes to 10 hours, even more preferably from 10 minutes to 5 hours, most preferably from 15 minutes to 1 hour and in particular from 20 to 40 minutes.

Before the reaction components are combined to produce the Eschenmoser salt, 3-methoxyacetophenone (I) may preferably be dissolved in a suitable solvent, it being possible to use, in particular, dimethylformamide, acetonitrile or isopropanol or mixtures of at least two of these solvents as a solvent. In a particularly preferred embodiment acetonitrile is used to dissolve the 3-methoxyacetophenone.

The solvent used to dissolve the 3-methoxyacetophenone (I) is preferably the same solvent in which the Eschenmoser salt is produced but may, however, also be different.

In a preferred embodiment the reaction components are combined in order to carry out the Mannich reaction, i.e. to unite the Eschenmoser salt and the 3-methoxyacetophenone (I), under reflux.

In another preferred embodiment the Mannich reaction is carried out at a reaction temperature preferably of from −10 to 100° C., more preferably from 0 to 80° C., even more preferably from 10 to 60° C., most preferably from 20 to 30° C. and in particular from 20 to 25° C.

In an embodiment of the process according to the invention the Mannich reaction may be started under reflux and, after a specific period of time, preferably after from 1 to 16 hours, even more preferably after from 2 to 14 hours, most preferably after from 4 to 10 hours and in particular after from 6 to 8 hours, the reaction mixture is cooled to a temperature preferably of from 20 to 25° C. (room temperature) and subsequently stirred at this temperature for a specific period of time, preferably for 1 to 30 hours, even more preferably for 2 to 24 hours, most preferably for 4 to 20 hours and in particular for 8 to 16 hours or 10 to 14 hours The total reaction time once the reaction components have been combined is preferably from 1 to 48 hours, more preferably from 4 to 40 hours, even more preferably from 8 to 32 hours, most preferably from 12 to 24 hours and in particular from 16 to 18 hours.

The reaction components of the Mannich reaction may be mixed into a suitable solvent and reacted. In this case the Eschenmoser salt is formed in situ and can then react with 3-methoxyacetophenone (I) under Mannich conditions.

This in situ Mannich reaction may also be carried out under the aforementioned conditions and using the aforementioned solvent.

The reaction mixture may preferably be cooled to 15° C., more preferably to 10° C., even more preferably to 5° C. and most preferably to 0° C. once the Mannich reaction has finished. The hydrochloride salt of the 3-dimethylamino-1-(3-methoxyphenyl)propan-1-one (II) may be precipitated from the reaction mixture which may preferably be isolated by means of filtration. The hydrochloride salt of compound (II) may then preferably be suspended or dissolved in an aqueous base in order to obtain the free base of the compound (II). Sodium hydroxide, sodium carbonate, sodium hydrogen carbonate, potassium hydroxide, potassium carbonate, potassium hydrogen carbonate, magnesium hydroxide, magnesium carbonate, calcium hydroxide or calcium carbonate or mixtures of at least two of these bases may preferably be used as bases. Aqueous sodium hydroxide solution is preferably used. The pH value is preferably set at 8 to 14, more preferably at 9 to 13, even more preferably at 10 to 12 and most preferably at 11 to 12.

The freed base of the 3-dimethylamino-1-(3-methoxyphenyl)propan-1-one (II) may then be extracted from the basic, aqueous solution, preferably using a suitable organic solvent. The extraction may be carried out with conventional organic solvents known to the person skilled in the art (for example chloroform, dichloromethane, diethylether, cyclohexane, methylcyclohexane, ethyl acetate, tert-butylmethyl ether or toluene). In a particularly preferred embodiment, extraction is carried out with toluene.

The resulting organic phase may then be dried, in particular over anhydrous magnesium or sodium sulfate or a mixture thereof, and then filtered. The organic solvent may preferably be separated using a rotary evaporator, for example at reduced pressure and an elevated temperature.

The resulting 3-dimethylamino-1-(3-methoxyphenyl)propan-1-one (II) may then be further purified, for example by means of flash chromatography or recrystallization. The 3-dimethylamino-1-(3-methoxyphenyl)propan-1-one (II) obtained once the organic phase has been removed may, however, also be used for the next reaction step, preferably without any further purification.

Reaction step (b) is preferably a Michael addition. Reaction step (c) is a cyclization reaction, preferably an intramolecular aldol reaction.

In a preferred embodiment of the process according to the invention, reaction steps (b) and (c) are carried out in a one-pot process (one-pot reaction), in which the product of the Mannich reaction, 3-dimethylamino-1-(3-methoxyphenyl)propan-1-one (II), is converted to 4-dimethylaminomethyl-3-hydroxy-3-(3-methoxyphenyl)cyclohexanone (IV). This means, that in this case only 4-dimethylaminomethyl-3-hydroxy-3-(3-methoxyphenyl)cyclohexanone (IV) is preferably obtained once the reaction has finished. The intermediate 2-dimethylaminomethyl-1-(3-methoxyphenyl)hexane-1,5-dione (III) formed during the one-pot reaction must thus preferably not be isolated and purified. The formation of the non-isolated intermediate (III) can be proven, for example by means of LC-MS (liquid chromatography-mass spectrometry).

The one-pot reaction may take place once the educt 3-dimethylamino-1-(3-methoxyphenyl)propan-1-one (II) has been dissolved in a suitable organic solvent, preferably in the presence of a base and an α,β-unsaturated ketone. Typical reaction conditions for this reaction are disclosed in the literature, for example in Turnbull et al., *Tetrahedron Lett.* 1984 (25) 5449-5452 and DeBoer, *J. Org. Chem.* 1974 (39) 2426-2427.

The sequence in which the reagents are added may vary in the case of the one-pot reaction. 3-dimethylamino-1-(3-methoxyphenyl)propan-1-one (II), the base and the α,β-unsaturated ketone may be present in a suitable solvent. The other two reagents may be added to this solution, for example simultaneously or in succession.

Tetrahydrofuran or toluene or a mixture thereof may preferably be used as a solvent in any ratio. Tetrahydrofuran is preferred. The solvents may also be used in anhydrous form. Alternatively, the solvent or mixture of solvents may contain from 0.10 to 10% by weight, more preferably from 0.50 to 7.5% by weight, even more preferably from 1.0 to 5.0% by weight, most preferably from 1.5 to 4.0% by weight and in particular from 2.0 to 3.0% by weight water. In a particularly preferred embodiment the solvent or mixture of solvents may contain 2.5±0.4% by weight water.

The reaction may also be carried out in a protective atmosphere, preferably in the presence of nitrogen or argon.

In a particularly preferred embodiment the base is first added to a solution of 3-dimethylamino-1-(3-methoxyphenyl)propan-1-one (II) in tetrahydrofuran. The solution is then preferably stirred for at least 1 minute, more preferably for at least 5 minutes, even more preferably for at least 10 minutes, most preferably for at least 15 minutes and in particular for at least 20 minutes. The α,β-unsaturated ketone is subsequently preferably added slowly to the reaction mixture, for example dropwise, over a period of time of preferably $\geq$10 minutes, more preferably $\geq$30 minutes, even more preferably $\geq$1 hour, most preferably $\geq$1.5 hours and in particular $\geq$2 hours. The α,β-unsaturated ketone may be dissolved before this addition, preferably in a suitable solvent, for example in tetrahydrofuran, toluene or a mixture of the two solvents in any ratio. The α,β-unsaturated ketone is preferably dissolved in the same solvent which is also used to dissolve the educt 3-dimethylamino-1-(3-methoxyphenyl)propan-1-one (II).

The substance amount of base used for reaction steps (b) and (c) may vary. 0.01 to 2.0 equivalents, more preferably 0.05 to 1.5 equivalents, even more preferably 0.10 to 1.0 equivalent, most preferably 0.15 to 0.75 equivalent and in particular 0.2 to 0.5 equivalent, based on the substance amount of 3-dimethylamino-1-(3-methoxyphenyl)propan-1-one (II) used, may be used for this.

The substance amount of α,β-unsaturated ketone used for reaction steps (b) and (c) may also vary. In this case, preferably 1 to 5 equivalents, more preferably 1 to 4 equivalents, even more preferably 1 to 3 equivalents, most preferably 1 to 2 and in particular 1 to 1.5 equivalents, based on the substance amount of 3-dimethylamino-1-(3-methoxyphenyl)propan-1-one (II) provided, may be used. The α,β-unsaturated ketone and 3-dimethylamino-1-(3-methoxyphenyl)propan-1-one (II) may also be used in substantially equimolar substance amounts (substance amount ratio=1:1).

In a preferred embodiment of the process according to the invention, the α,β-unsaturated ketone is methyl vinyl ketone.

For reaction steps (b) and (c), 1,8-diazabicyclo[5.4.0]undec-7-ene (DBU), sodium hydride (NaH), NaOH, KOH, amines, in particular tri-$C_{1-4}$ alkyl amines, such as triethylamine, sodium methanolate or potassium-tert-butylate (KOtBu) or mixtures of at least two of the bases mentioned may preferably be used as a base. Sodium hydride, KOH, potassium-tert-butylate or a mixture of at least two of these bases, in particular potassium-tert-butylate, is particularly preferably used as a base in the process according to the invention.

The reaction temperature for the one-pot reaction is preferably from −70 +70° C., more preferably from −60 to 60° C., even more preferably from −50 to 50° C., most preferably from −40 to 40° C. and in particular from −30 to 20° C.

During the one-pot reaction, two secondary reactions may possibly take place depending on the reaction temperature and the solvent and base used. In this case, on the one hand, the dimethylamino substituents are eliminated from 3-dimethylamino-1-(3-methoxyphenyl)propan-1-one (II), 1-(3-methoxyphenyl)propyl-2-en-1-one being formed as a by-product, and on the other hand, water is eliminated from 4-dimethylaminomethyl-3-hydroxy-3-(3-methoxyphenyl) cyclohexanone (IV), 4-dimethylaminomethyl-3-(3-methoxyphenyl)cyclohex-2-enone being formed as a by-product.

Surprisingly, it has been found that when using preferably $\leq$0.8 equivalent, more preferably $\leq$0.6 equivalent, even more preferably $\leq$0.4 equivalent and in particular $\leq$0.3 equivalent of base, in particular potassium-tert-butylate, in each case based on the substance amount of 3-dimethylamino-1-(3-methoxyphenyl)propan-1-one (II) used, preferably in tetrahydrofuran and at a reaction temperature of preferably $\leq$0° C., more preferably $\leq$−5° C. or $\leq$−10° C., even more preferably $\leq$−15° C. or $\leq$−20° C., most preferably $\leq$−25° C. and in particular $\leq$−30° C., the formation of by-products can be minimized or even almost completely eliminated.

In a preferred embodiment of the one-pot reaction, preferably from 0.1 to <0.25, more preferably from 0.15 to 0.24, even more preferably from 0.15 to 0.23, most preferably from 0.15 to 0.2 equivalent potassium-tert-butylate, based on the substance amount of 3-dimethylamino-1-(3-methoxyphenyl) propan-1-one (II) used, is first added to a solution of 3-dimethylamino-1-(3-methoxyphenyl)propan-1-one (II) in tetrahydrofuran, and a diluted solution of methyl vinyl ketone in tetrahydrofuran is then slowly added over 1.2 to 1.4 hours to the reaction solution at a temperature of, at most, −30° C.

Once the methyl vinyl ketone has been added, the reaction mixture is subsequently stirred, preferably for up to 12 hours, more preferably for up to 10 hours, even more preferably for up to 8 hours, most preferably for up to 6 hours and in particular for up to 4 hours. The temperature may, in this case, preferably be $\leq$0° C., more preferably $\leq$−5° C., even more preferably $\leq$−15° C., most preferably $\leq$−25° C. and in particular $\leq$−30° C. In a preferred embodiment the temperature is between −30° C. and −35° C.

The reaction can be slowed down, for example by adding an aqueous acid to the reaction solution, preferably by adding aqueous phosphoric acid, the corresponding acid addition salt precipitating from the solution. The salt obtained may subsequently be separated off, for example by means of filtration, and after treatment with an aqueous alkali solution, for example sodium hydroxide solution, the free base of compound (IV) may be obtained.

The freed base of compound (IV) may then be extracted from the basic, aqueous solution using a suitable organic solvent. This extraction may be carried out with conventional organic solvents known to the person skilled in the art (for example chloroform, dichloromethane, diethyl ether, tert-butylmethyl ether, toluene or ethyl acetate). In a particularly preferred embodiment extraction is carried out with ethyl acetate.

The organic solvent may then be dried over anhydrous magnesium or sodium sulfate or a mixture thereof and subsequently filtered. The organic solvent may then be separated off using a rotary evaporator, for example at reduced pressure and a raised temperature.

The resulting crude product of 4-dimethylaminomethyl-3-hydroxy-3-(3-methoxyphenyl)cyclohexanone (IV) may then be further purified, for example by means of column chromatography or recrystallization. The crude product obtained once the organic phase has been removed may, however, be used for the next reaction step owing to the high reaction selectivity and high yield, preferably without any further purification.

Reaction step (d) is preferably a reduction, more preferably a diastereoselective reduction.

In a preferred embodiment of the process according to the invention, the educt 4-dimethylaminomethyl-3-hydroxy-3-(3-methoxyphenyl)cyclohexanone (IV) is dissolved in a suitable solvent and the reducing agent is subsequently added to this solution. The reducing agent may preferably be dissolved in a suitable solvent or suspended before this addition or even added directly.

In another preferred embodiment of the process according to the invention the reducing agent is dissolved in a suitable solvent or suspended, and the educt 4-dimethylaminomethyl- 3-hydroxy-3-(3-methoxyphenyl)cyclohexanone (IV), which is preferably present either dissolved in a suitable solvent or undissolved in its pure form, is subsequently added to the solution or suspension of the reducing agent.

Methanol, ethanol, isopropanol or tetrahydrofuran, particularly preferably tetrahydrofuran, may, for example, be used as suitable solvents for 4-dimethylaminomethyl-3-hydroxy-3-(3-methoxyphenyl)cyclohexanone (IV). Any mixture of the aforementioned solvents in any ratio is also possible.

Low-molecular weight alcohols, such as methanol, ethanol, n-propanol or isopropanol, may in particular be used as a suitable solvent for the reducing agent. Ethanol or methanol is preferably used, more preferably ethanol, to dissolve or suspend the reducing agent. Any mixture of the aforementioned solvents in any ratio may also be used.

In a preferred embodiment a metal hydride, such as sodium borohydride, lithium borohydride or diisobutylaluminium hydride, is used as a reducing agent. Sodium borohydride may particularly preferably be used.

Surprisingly, it has been found that using the achiral reducing agent sodium borohydride in particular leads to a diastereoselective reduction which ensures a high stereoisomer purity of the desired product (1RS,3RS,6RS)-6-dimethylaminomethyl-1-(3-methoxyphenyl)-cyclohexane-1,3-diol (Va and Vb).

The diastereoisomeric ratio is, in this case, preferably $\geq 55:45$, more preferably $\geq 60:40$, even more preferably $\geq 65:35$ or $\geq 70:30$, most preferably $\geq 75:25$ and in particular $\geq 80:20$.

The diastereomeric ratio (dr) is, in this case, preferably defined as the percentage of diastereomers (Va) and (Vb) to the percentage of undesirable diastereomers, such as (Vc), (Vd), (Ve), (Vf), (Vg) and (Vh), in each case based on the total product mixture (see IUPAC Compendium of Chemical Terminology, second edition, 1997). Within the context of the description, a diastereomeric ratio of, for example, 80:20 means that 80% of the total product mixture consists of diastereomers (Va) and (Vb).

In a preferred embodiment of the process according to the invention 4-dimethylaminomethyl-3-hydroxy-3-(3-methoxyphenyl)cyclohexanone) (IV) is dissolved in tetrahydrofuran and a solution of sodium borohydride in ethanol is then added to this solution.

In another preferred embodiment of the process according to the invention the reducing agent sodium borohydride is provided in ethanol and a solution of 4-dimethylaminomethyl-3-hydroxy-3-(3-methoxyphenyl)cyclohexanone (IV) in tetrahydrofuran is then added to this ethanolic mixture. Anhydrous tetrahydrofuran may also be used which, for example, may be obtained by distilling the tetrahydrofuran over benzophenone/sodium in a suitable anhydrous apparatus in a dry protective atmosphere.

The temperature of the reaction solution may, irrespective of whether the educt or reducing agent is present, preferably be $\leq 30°$ C., more preferably $\leq 20°$ C., even more preferably $\leq 10°$ C., most preferably $\leq 0°$ C. and in particular $\leq -10°$ C.

The educt or reducing agent may be added in such a way that, owing to the exothermic reduction reaction, the reaction mixture does not heat up excessively. This may preferably be achieved by adequately cooling the reaction mixture. This cooling process preferably ensures that the temperature of the reaction mixture when combining the co-reactants is preferably increased by at most $+20°$ C., more preferably by at most $+15°$ C., even more preferably by at most $+10°$ C. and most preferably by at most $+5°$ C. The co-reactants may also be combined in such a way that the reaction temperature does not increase during the addition process.

Once the co-reactants, i.e. the educt (IV) and the reducing agent, have been completely combined, the reaction mixture may be subsequently stirred, preferably for $\leq 24$ hours, more preferably for $\leq 18$ hours, even more preferably for $\leq 12$ hours, most preferably for $\leq 8$ hours and in particular for $\leq 4$ hours In comparison with the temperature which is selected while the co-reactants are combined, subsequent stirring is preferably carried out at a higher temperature. In this case the temperature may preferably be set at $-10°$ C. to $50°$ C., more preferably at $-5°$ C. to $30°$ C., even more preferably at $-2°$ C. to $20°$ C., most preferably at $0°$ C. to $10°$ C. and in particular at $3°$ C. to $6°$ C.

The reduction reaction is slowed down, preferably by adding an aqueous acid to the reaction solution, for example aqueous ammonium chloride solution, and during this process any excess reducing agent for example is also destroyed. This process may take place with a simultaneous cooling of the reaction mixture to preferably $\leq 10°$ C., more preferably $\leq 0°$ C. and even more preferably to $\leq -10°$ C.

Aqueous alkaline solution, for example aqueous sodium hydroxide solution, may be added to the product solution once the reaction has been slowed and the product solution is preferably adjusted to an alkaline pH value in order to be able to extract the free base of compound (V) from the solvent. After the subsequent extraction, the organic phase is preferably dried over anhydrous magnesium or sodium sulfate, filtered and evaporated (for example in a rotary evaporator). The residue thus obtained once the solvent has been removed may subsequently be purified, for example by means of column chromatography.

The undesired stereoisomers (Vc) to (Vh) may be separated, for example by preparative liquid chromatography, preferably by means of preparative HPLC (high performance liquid chromatography). Furthermore, the product mixture may preferably be subjected to fractionated crystallization in order to separate the undesirable stereoisomers of compound (V). Other methods for purifying chiral compounds are known to the person skilled in the art.

Furthermore, the desired enantiomers (1R,3R,6R)-6-dimethylaminomethyl-1-(3-methoxyphenyl)cyclohexane-1,3-diol (Va) and (1S,3S,6S)-6-dimethylaminomethyl-1-(3-methoxyphenyl)cyclohexane-1,3-diol (Vb) may be present in any ratio once the mixture of enantiomers has been purified. However, the two enantiomers may also be separated from one another in such a way that, once the enantiomers have been separated, both the enantiomer (Va) and the enantiomer (Vb) are present in a preferably enantiomer-pure state. Methods for separating enantiomers are known to the person skilled in the art. In particular, the compounds (1R,3R,6R)-6-dimethylaminomethyl-1-(3-methoxyphenyl)cyclohexane-1,3-diol (Va) and (1S,3S,6S)-6-dimethylaminomethyl-1-(3-methoxyphenyl)cyclohexane-1,3-diol (Vb) are obtained in the form of their substantially racemic mixture.

The optional reaction step(s) correspond(s) with the production of an acid addition salt, which preferably takes place by adding a suitable acid to the free base of the enantiomer-pure compounds (Va) or (Vb) or a mixture thereof.

For this reaction step the aforementioned free base of the enantiomer-pure compounds (Va) or (Vb) or a mixture thereof may be present preferably dissolved in a suitable organic solvent.

Conventional solvents known to persons skilled in the art may be used as a suitable solvent, in which the free base is soluble but the corresponding acid addition salt is only soluble to a degree or is insoluble. In particular, the solvents acetone, benzene, n-butanol, tert-butyl methyl ether, chloroform, cyclohexane, diethyl ether, 1,4-dioxane, ethyl acetate, ethanol, hexane, heptane, isopropanol, methanol, methylene chloride, pentane, petroleum ether, n-propanol, tetrahydrofuran or toluene are suitable. Any mixture of the aforementioned solvents in any ratio may also be used. The use of ethyl acetate is particularly preferred.

Precipitation or crystallization of the acid addition salt may preferably be initiated or improved by cooling the reaction solution and, optionally, by additionally reducing the reaction solution, for example by evaporating some of the solvent in the rotary evaporator. The resulting precipitate may then be filtered out and, optionally, washed using a suitable liquid in which the residue is only slightly soluble or even insoluble. Further purification may preferably take place by means of recrystallization.

In order to produce the suitable pharmaceutically acceptable acid addition salts, the following inorganic and/or organic acids may preferably be used, for example acetic acid, 2,2-dichloroacetic acid, acylated amino acids, preferably acetylated amino acids, such as N-acetyl alanine, N-acetyl cysteine, N-acetyl glycine, N-acetyl isoleucine, N-acetyl leucine, N-acetyl methionine, N-acetyl phenyl alanine, N-acetyl proline, N-acetyl serine, N-acetyl threonine, N-acetyl tyrosine, N-acetyl valine, adipic acid, alginic acid, ascorbic acid, L-aspartic acid, benzene sulfonic acid, benzoic acid, 4-acetamidobenzoic acid, (+)-camphoric acid, (−)-camphoric acid, (+)-camphor sulfonic acid, (−)-camphor sulfonic acid, (+)-camphor-10-sulfonic acid, (−)-camphor-10-sulfonic acid, (±)-camphor-10-sulfonic acid, capric acid, caproic acid, caprylic acid, cationic exchanger resins, cinnamic acid, citric acid, cyclohexyl sulfamic acid, sulfuric acid monodecyl ester, ethane-1,2-disulfonic acid, ethanesulfonic acid, 2-hydroxyethanesulfonic acid, formic acid, fumaric acid, mucic acid (galactosaccharic acid), gentisic acid, glucose monocarboxylic acid (glucoheptanoic acid), D-gluconic acid, D-glucuronic acid, L-glutamic acid, α-oxoglutaric acid (α-ketoglutaricacid), hydroxyacetic acid (glycolic acid), hippuric acid (N-benzoylglycine), hydrogen bromide, hydrogen chloride, (+)-L-lactic acid, (±)-DL-lactic acid, lactobionic acid (4-O-β-D-galactopyranosyl-D-gluconic acid), maleic acid, (−)-L-malic acid, malonic acid, (±)-DL-mandelic acid, methane sulfonic acid, naphthalin-2-sulfonic acid, naphthalin-2,5 disulfonic acid, 1-hydroxy-2-naphthalincarboxylic acid, nicotinic acid, nitric acid, oleic acid, acid whey (orotic acid, uracil-6-carboxylic acid), oxalic acid, palmitic acid, pamoic acid (embonic acid), phosphoric acid, L-pyroglutamic acid, salicylic acid, acetylsalicylic acid, 4-aminosalicylic acid, sebacic acid, stearic acid, succinic acid, sulfuric acid, tannic acid, (+)-L-tartaric acid, (±)-DL-tartaric acid, thiocyanic acid, p-toluene sulfonic acid and undecylenic acid. Preferred salts are hydrochloride, saccharinate, dihydrogen phosphate, hydrogen phosphate and phosphate. The phosphate salt of (1RS,3RS,6RS)-6-dimethylaminomethyl-1-(3-methoxyphenyl)-cyclohexane-1,3-diol is particularly preferred.

The product according to the invention may preferably also be present as a mixture of the salts of the aforementioned organic and inorganic acids in any ratio.

The invention will be described in further detail hereinafter with reference to illustrative examples of preferred embodiments, but its disclosure is not limited thereto.

EXAMPLES 3-dimethylamino-1-(3-methoxyphenyl)-propan-1-one (II)

The Eschenmoser salt was produced by reacting 232 g (2.27 mol, 1 equivalent) tetramethyl diaminomethane with 187 g (2.14 mol, 0.95 equivalent) acetyl chloride in 1200 ml acetonitrile. 328 g (2.17 mol, 0.96 equivalent) 3-methoxyacetophenone were then added within 115 minutes at a temperature of from +3° C. to +11° C. and then stirred at from +20° C. to +25° C. for 20 to 21 hours. The resulting hydrochloride salt of the 3-dimethylamino-1-(3-methoxyphenyl)-propan-1-one (II) was filtered out. The residue was suspended in 1600 ml water and 190 ml sodium hydroxide solution (36% by weight) (pH 11-12) and extracted with 1000 ml ethyl acetate. The organic phase was separated off and dried over 50 g sodium sulfate. Once the organic solvent had been evaporated, the free base of the 3-dimethylamino-1-(3-methoxyphenyl)-propan-1-one (II) was obtained as a colorless oil (93% yield, 96% purity ascertained by HPLC).

$^{13}$C NMR (100 MHz, CDCl$_3$): $\delta_{ppm}$ 199.0, 159.8, 138.3, 120.7, 119.6, 112.2, 77.4, 76.8, 55.4, 54.4, 45.6, 37.1.

4-dimethylaminomethyl-3-hydroxy-3-(3-methoxyphenyl)-cyclohexanone (IV)

The influence of the base used, the solvent and temperature on the reaction profile was examined. The results are summarized in the following table:

| Ex. No. | Solvent | Base | Temperature | Product(s) |
|---|---|---|---|---|
| 1 | THF | 0.25 eq DBU | 20° C. | 47% (II) |
|   |   |   |   | 42% (II-NMe$_2$) |
| 2 | THF | 0.25 eq KOtBu | 20° C. | 66% (IV-H$_2$O) |
| 3 | toluene | 0.25 eq DBU | 20° C. | 33% (II) |
|   |   |   |   | 58% (II-NMe$_2$) |
| 4 | toluene | 0.25 eq KOtBu | 20° C. | 69% (IV-H$_2$O) |
| 5 | THF | 0.05 eq KOtBu | 20° C. | 45% (II) |
|   |   |   |   | 21% (III) |
|   |   |   |   | 16% (IV) |
|   |   |   |   | 6% (IV-H$_2$O) |
| 6 | THF | 0.25 eq KOtBu | −30° C. | 77% (II) |
|   |   |   |   | 8% (IV) |
| 7 | THF | 0.05 eq KOtBu | −30° C. | 60% (II) |
|   |   |   |   | 28% (III) |
|   |   |   |   | 6% (IV) |
| 8 | THF | 1.0 eq KOtBu | −30° C. | 95% (II) |
| 9 | THF | 1.0 eq NaH | −30° C. | 97% (II) |
| 10 | THF | 0.2 eq KOtBu | −30° C. | (IV) |

Abbreviations: THF: tetrahydrofuran; eq: equivalent(s); DBU: 1.8-diazabicyclo[5.4.0]undec-7-ene; KOtBu: potassium-tert-butylate, NaH: sodium hydride; (II): 3-dimethylamino-1-(3-methoxyphenyl)-propan-1-one; (II-NMe$_2$): elimination product of (II)=1-(3-methoxyphenyl)prop-2-en-1-one; (III): 2-dimethylaminomethyl-1-(3-methoxyphenyl)-hexane-1,5-dione; (IV): 4-dimethylaminomethyl-3-hydroxy-3-(3-methoxyphenyl)-cyclohexanone; (IV-H$_2$O): elimination product of (IV)=4-[(dimethylamino)methyl]-3-(3-methoxyphenyl)cyclohex-2-enone.

HPLC analysis: The table shows the surface area of the respective educt, product or by-product in percent ascertained by HPLC analysis. In this case, 200 μl of the reaction solution was removed after 30 minutes and diluted with acetonitrile:acetic acid (10%)=1:1. The surface areas of the individual peaks were ascertained at a wavelength of 220 nm.

Example Nos. 1-7

1 equivalent methyl vinyl ketone was added to a solution of 3-dimethylamino-1-(3-methoxyphenyl)-propan-1-one (II) in THF or toluene. The resulting solution was brought to the respective reaction temperature and the base DBU, KOtBu or NaH was added.

Example No. 8

KOtBu was first added to the educt solution at −30° C. Methyl vinyl ketone was then added, also at −30° C.

Example No. 9

NaH was first added to the educt solution at 20° C. Methyl vinyl ketone was then added at −30° C.

Example No. 10

KOtBu was first added to the educt solution at −30° C. 1.2 equivalents methyl vinyl ketone, which had previously been dissolved in THF, were then added slowly over 1.5 hours. The reaction was slowed by adding aqueous ammonium chloride solution. After aqueous work-up (IV) was obtained as a yellow oil.

Result: At a reaction temperature of −30° C., conversion was lower than at 20° C. (Example Nos. 2/6 and 5/7), but there was no elimination of (IV) to (IV-H$_2$O). Reversing the sequence of adding the base and methyl vinyl ketone did not lead to any significant conversion to (IV) (Example Nos. 9 and 10). Free methyl vinyl ketone could not be found in any of the samples taken of the reaction solutions. This result suggests that the methyl vinyl ketone was completely consumed, even though conversion to (IV) was low. This may be explained by a complete polymerization of the methyl vinyl ketone at higher concentrations. By slowly adding the methyl vinyl ketone solution dropwise to the reaction mixture, polymerization could be avoided as much as possible and the product yield was high (Example No. 10).

Synthesis was, for the most part, carried out similarly to the synthesis description of Ex. No. 10.

Synthesis procedure: 10 g (0.048 mol, 1 equiv.) 3-dimethylamino-1-(3-methoxyphenyl)-propan-1-one (II) and 50 ml anhydrous tetrahydrofuran were placed in an anhydrous, dried three-necked flask with a dropping funnel. The resulting yellow solution was cooled to −10° C. to −15° C. A solution of 1.1 g (0.0098 mol, 0.2 equiv.) KOtBu in 25 ml tetrahydrofuran was added dropwise within 10 minutes at −10° C. to −15° C. Freshly distilled methyl vinyl ketone (4.1 g; 0.058 mol, 1.21 equiv.) was then added dropwise within 110 minutes at −13° C. to −18° C. Once all the methyl vinyl ketone had been added, the educt (II) could no longer be found in the reaction mixture. 35 ml 15% phosphoric acid was then added dropwise at −10° C. to −15° C. and the reaction mixture was warmed to room temperature. The resulting precipitate was sharply suction-filtered using a Nutsch filter (G3). The resulting phosphate salt was dissolved in 100 ml water and converted into the corresponding free base by adding 4 ml 32% sodium hydroxide solution (pH 11-12). The aqueous solution was extracted twice, each time with 30 ml ethyl acetate. The combined organic phases were dried over sodium sulfate and evaporated under vacuum. The title compound was obtained at an 85% yield and with a purity of 83% (HPLC).

(1RS,3RS,6RS)-6-dimethylaminomethyl-1-(3-methoxyphenyl)-cyclohexane-1,3-diol (V)

A solution of 10 g (0.036 mol) of the crude product (IV) in 36.5 ml tetrahydrofuran was added dropwise at +2° C. with stirring to a solution of 1.36 g (0.036 mol, 1 equiv.) sodium borohydride in 15 ml ethanol and 36.5 ml tetrahydrofuran. Once the crude product solution had been completely added the mixture was then stirred for 60 to 90 minutes at +15° C. 25 ml aqueous ammonium chloride solution (10% w/w) were then added and alkalized with 5 ml sodium hydroxide solution (32%) to pH 12. After being extracted twice with 50 ml ethyl acetate, the combined phases were dried over magnesium sulfate and evaporated in vacuo. 10 g crude mixture was obtained in this case.

Acid Addition Salt

In a 250 ml round-bottomed flask, 17.5 g (0.062 mol) (1RS,3RS,6RS)-6-dimethylaminomethyl-1-(3-methoxyphenyl)-cyclohexane-1,3-diol (V) was suspended in 55 ml ethanol and mixed with diluted phosphoric acid (7.33 g 89% phosphoric acid in 45 ml water). The batch was seeded to crystallization and stirred at 5 to 7° C. for 3.5 hours. The crystals obtained were then suction-filtered over a G3 sintered-glass filter and oven-dried at 60 to 80 mbar/40 to 45° C. for 16 hours. The racemate of (1RS,3RS,6RS)-6-dimethylaminomethyl-1-(3-methoxyphenyl)-cyclohexane-1,3-diol was obtained in a yield of 46%.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A process for producing (1R,3R,6R)-6-dimethylaminomethyl-1-(3-methoxyphenyl)-cyclohexane-1,3-diol, (1S,3S,6S)-6-dimethylaminomethyl-1-(3-methoxyphenyl)-cyclo-hexane-1,3-diol, a mixture thereof, or an acid addition salt thereof, said process comprising:

reacting 3-dimethylamino-1-(3-methoxyphenyl)-propan-1-one (II)

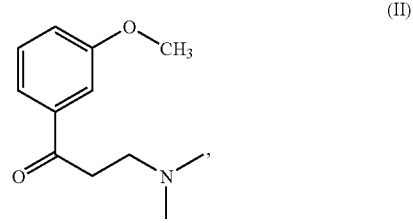

(II)

with an α,β-unsaturated ketone to form 2-dimethylaminomethyl-1-(3-methoxyphenyl)hexane-1,5-dione (III)

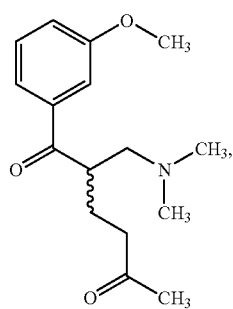

and cyclizing the 2-dlimethylaminomethyl-1-(3-methoxyphenyl)hexane-1,5-dione (III) to form 4-dimethylaminomethyl-3-hydroxy-3-(3-methoxyphenyl)cyclohexanone (IV)

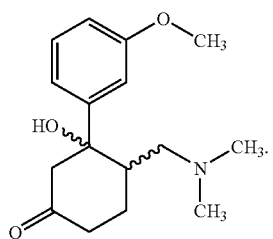

2. A process according to claim 1, further comprising reacting 3-methoxyaceto-phenone (I)

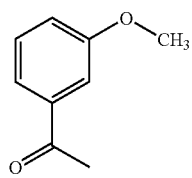

with an Eschenmoser salt to form the 3-dimethylamino-1-(3-methoxyphenyl)-propan-1-one (II)

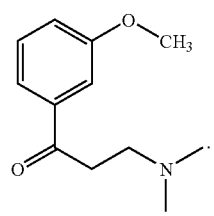

3. A process according to claim 1, further comprising:
reducing the 4-dimethylaminomethyl-3-hydroxy-3-(3-methoxyphenyl)cyclohexanone (IV) to form (1R,3R,6R)-6-dimethylaminomethyl-1-(3-methoxyphenyl)-cyclo-hexane-1,3-diol) (Va) or (1S,3S,6S)-6-dimethylaminomethyl-1-(3-methoxy-phenyl)-cyclohexane-1,3-diol (Vb) or a mixture thereof

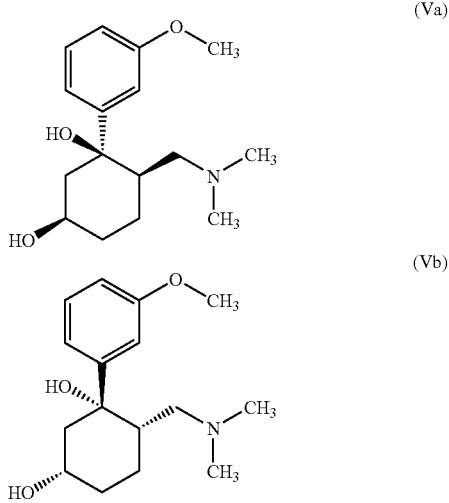

and optionally reacting the (1R,3R,6R)-6-dimethylaminomethyl-1-(3-methoxyphenyl)cyclo-hexane-1,3-diol (Va) or (1S,3S,6S)-6-dimethylaminomethyl-1-(3-methoxyphenyl)-cyclohexane-1,3-diol (Vb) or a mixture thereof with an acid to form the corresponding acid addition salt or salts.

4. A process according to claim 2, wherein the reacting of 3-methoxyacetophenone (I) is carried out as a Mannich reaction.

5. A process according to claim 4, wherein the 3-methoxyacetophenone (I) is reacted with an Eschenmoser salt formed from tetramethyl diaminomethane and acetyl chloride.

6. A process according to claim 1, wherein the reacting of 3-dimethylamino-1-(3-methoxyphenyl)-propan-1-one (II) is carried out as a Michael addition.

7. A process according to claim 1, wherein the reacting of 3-dimethylamino-1-(3-methoxyphenyl)-propan-1-one (II) and the cyclizing of 2-dimethylaminomethyl-1-(3-methoxyphenyl)hexane-1,5-dione (III) are carried out in a one-pot reaction.

8. A process according to claim 1, wherein 3-dimethylamino-1-(3-methoxyphenyl)-propan-1-one (II) is reacted with a base and methyl vinyl ketone.

9. A process according to claim 8, wherein the base is selected from the group consisting of NaOH, KOH, Tri-$C_{1-4}$ alkyl amines, sodium methanolate, potassium-tert-butylate, 1,8-diazabicyclo[5.4.0]undec-7-ene (DBU) and sodium hydride.

10. A process according claim 3, wherein sodium borohydride, lithium borohydride or diisobutylaluminium hydride is used as a reducing agent.

11. A process according to claim 1, wherein a substantially racemic mixture of (1R,3R,6R)-6-dimethylaminomethyl-1-(3-methoxyphenyl)cyclohexane-1,3-diol) (Va) and (1S,3S,6S)-6-dimethylaminomethyl- 1-(3-methoxyphenyl)cyclohexane-1,3-diol (Vb) or of the acid addition salts thereof is obtained.

12. A process according to claim 1, wherein a phosphate acid addition salt is obtained.

* * * * *